(12) United States Patent
Anayama et al.

(10) Patent No.: US 8,977,580 B2
(45) Date of Patent: Mar. 10, 2015

(54) DEFECT CLASSIFICATION APPARATUS

(75) Inventors: Kazunori Anayama, Tokyo (JP);
Tetsuya Yadoguchi, Tokyo (JP);
Toshiyuki Suzuma, Tokyo (JP); **Eiji
Honda, Tokyo (JP); Takahiro Okada**,
Tokyo (JP); Shinya Yoshikawa, Tokyo
(JP); Tamotsu Nishimine, Tokyo (JP)

(73) Assignee: **Nippon Steel & Sumitomo Metal
Corporation**, Tokyo (JP)

( * ) Notice: Subject to any disclaimer, the term of this patent is extended or adjusted under 35 U.S.C. 154(b) by 313 days.

(21) Appl. No.: 13/703,536

(22) PCT Filed: Jun. 8, 2011

(86) PCT No.: PCT/JP2011/063119
§ 371 (c)(1),
(2), (4) Date: Mar. 7, 2013

(87) PCT Pub. No.: WO2011/158711
PCT Pub. Date: Dec. 22, 2011

(65) Prior Publication Data
US 2013/0173508 A1 Jul. 4, 2013

(30) Foreign Application Priority Data
Jun. 14, 2010 (JP) .................................. 2010-135218

(51) Int. Cl.
*G06F 15/18* (2006.01)
*G06N 99/00* (2010.01)
(Continued)

(52) U.S. Cl.
CPC ............ *G06N 99/005* (2013.01); *G01N 21/892* (2013.01); *G01N 21/952* (2013.01);
(Continued)

(58) Field of Classification Search
CPC .......... G06F 15/18; G01N 2021/8918; G01N 21/892; G01N 21/952; G06T 2207/20081
USPC .......................................................... 706/12
See application file for complete search history.

(56) References Cited

U.S. PATENT DOCUMENTS 6,246,787 B1 * 6/2001 Hennessey et al. ........... 382/141
2004/0252878 A1 * 12/2004 Okuda et al. ................. 382/145
(Continued)

FOREIGN PATENT DOCUMENTS

JP 2009-186243 A 8/2009
JP 2009-281742 A 12/2009

OTHER PUBLICATIONS

International Search Report issued in PCT/JP2011/063119, mailed on Jul. 26, 2011.

*Primary Examiner* — Kakali Chaki
*Assistant Examiner* — Peter Coughlan
(74) *Attorney, Agent, or Firm* — Birch, Stewart, Kolasch & Birch, LLP

(57) ABSTRACT

The present invention has its objective to provide a defect classification apparatus which suppresses over-fitting and accurately classify the defect type of a defect. A defect classification apparatus is provided in which a data point indicating feature information of a defect to be classified having an unknown defect type is mapped to a point in a mapping space having a dimensional number higher than the number of features constituting the feature information, and the defect type of the defect to be classified is classified based on in which of two regions of defect type, which are formed by separating the mapping space by a decision boundary, the mapped point is located, wherein a discriminant function indicating the decision boundary is determined by adopting a weight which minimizes the sum of the classification error, which corresponds to the accuracy in classifying a training defect dataset, and a regularization term, which has a positive correlation with the dimensional number of the decision boundary, as the weight for each feature constituting the discriminant function.

4 Claims, 5 Drawing Sheets

(51) Int. Cl.
*G01N 21/892* (2006.01)
*G01N 21/952* (2006.01)
*G06T 7/00* (2006.01)
*G01N 21/89* (2006.01)

(52) U.S. Cl.
CPC ...... *G06T 7/0004* (2013.01); *G01N 2021/8918* (2013.01); *G06T 2207/20081* (2013.01); *G06T 2207/30136* (2013.01)

USPC .......................................................... 706/12

(56) References Cited

U.S. PATENT DOCUMENTS

2005/0177040 A1* 8/2005 Fung et al. .................... 600/407
2005/0285588 A1* 12/2005 Katragadda et al. .......... 324/126
2007/0176312 A1* 8/2007 Clark et al. .................. 264/40.1

* cited by examiner

Figure 2

| Identifier | Feature information ||| Defect type |
|---|---|---|---|---|
| | Feature (size) | Feature (area) | Feature (Brightness) | |
| 001 | 0.1 | 0.5 | 0.8 | A |
| 002 | 0.5 | 0.1 | 0.5 | B |
| 003 | 0.2 | 0.6 | 0.9 | A |
| 004 | 0.3 | 0.5 | 0.9 | B |
| ⋮ | ⋮ | ⋮ | ⋮ | ⋮ | ated in priori by the defect classification apparatus of Patent
DEFECT CLASSIFICATION APPARATUS

TECHNICAL FIELD

The present invention relates to a defect classification apparatus for classifying defect types of a defect. Particularly, the present invention relates to a defect classification apparatus which is suitable for use in classifying defect types of a defect that occurs on rolling products (such as a wire rod, tube, and sheet material) made of metal (for example, steel material).

BACKGROUND ART

For example, in a manufacturing line of wire rod, a defect classification apparatus is used with image processing on a grabbed image sequence of wire rod grabbed by a camera placed in the manufacturing line to classify defect types of a defect such as a crack on the wire rod. The defect classification apparatus determines a defect region corresponding to a defect that has occurred in a wire rod from in the grabbed image sequence, and classify the defect type of the defect from features (such as the size and area) of the defect region.

In the defect classification apparatus of Patent Literature 1, a mapping space, which is a higher dimension than feature information (a vector) whose components include a plurality of features (for example, the size and the area of a defect) indicating attributes of a defect to be classified having an unknown defect type is classified into two regions of defect type by a decision boundary. This decision boundary is created in priori by the defect classification apparatus of Patent Literature 1 by using the feature information of a training defect dataset of the two defect types of which defect type is labeled by a user. In the defect classification apparatus of Patent Literature 1, a data point (a point at the tip of a vector) indicating feature information of a defect to be classified is mapped into the mapping space, and unknown defect type of the defect to be classified will be classified to the defect type corresponding to the region where the mapped data point (hereafter, referred to as a "mapped point") is located.

The defect classification apparatus of Patent Literature 1 creates a decision boundary such that when the defect type of each training defect dataset is classified, the defect type of each training defect dataset is correctly classified (as classified by a user) by a similar method (a method of mapping a data point indicating feature information into a mapping space, and classifying the defect type in accordance with the region in which the mapped point is located) as that for classification of the defect types of a defect to be classified. Among training defect dataset used for the creation of a decision boundary, there is a training defect dataset whose feature has a singular value, and the position of mapped point of which is significantly different from that of a training defect dataset whose feature does not have a singular value. The defect classification apparatus of Patent Literature 1 creates a decision boundary such that the defect type of each training defect dataset is correctly classified. As a result, a decision boundary which is over-fitted to the feature information of the training defect dataset which is used for creating the decision boundary will have been created, resulting in over-fitting which is a phenomenon that the ability to cope with a defect to be classified having an unknown defect type is deteriorated. If over-fitting occurs when there is a training defect dataset whose feature has a singular value, a decision boundary having an overly increased dimensional number is created such that the defect type is accurately judged even for the training defect dataset whose feature has a singular value. If such over-fitting occurs, there may be a case in which the defect type of a defect to be classified having an unknown defect type cannot be accurately classified.

CITATION LIST

Patent Literature

[Patent Literature 1] JP2009-186243A

SUMMARY OF INVENTION

Technical Problem

Accordingly, the present invention has its objective to provide a defect classification apparatus which suppresses over-fitting and accurately classifies the defect type of a defect.

Solution to Problem

The present invention provides a defect classification apparatus in which a data point indicating feature information whose components include a plurality of features indicating attributes of a defect to be classified having an unknown defect type is mapped to a point in a mapping space which has a dimensional number higher than the number of the features constituting the feature information, and determination is made as to which of two regions of defect type, which are formed by separating the mapping space, contains the mapped point to classify the defect type of the defect to be classified to be the defect type corresponding to the region where the mapped point is located, the defect classification apparatus comprising:

an extraction section for extracting the feature information; a determination section for determining a discriminant function indicating a decision boundary which separates the mapping space; and a classification section for classifying the defect type of the defect to be classified based on an output value of the discriminant function when the feature information of the defect to be classified is inputted into the discriminant function determined by the determination section, wherein each of the two defect types is a predetermined and mutually different defect type, the determination section determines the discriminant function by using the feature information of training defect dataset which is known to have either of the two defect types, the discriminant function is a function that consists of a kernel function (x, x') which outputs a mapped point of a training defect dataset whose feature information is inputted when feature information of the training defect dataset of either one or the other defect type of the two defect types is inputted, and the weight of each feature constituting the feature information, which is attached to the kernel function k(x, x'), and the kernel function (x, x') is a kernel function in which a matrix K whose elements are given as k(x, x') is positive semi-definite, x is feature information of the training defect dataset of the one defect type, and x' is feature information of the training defect dataset of the other defect type, wherein the determination section determines the weight of each feature constituting the feature information for a predetermined regularization parameter so as to minimize the value of an error function, which consists of a sum of: classification error which is defined by the difference between the output value of the discriminant function when the feature information of a training defect dataset of the one defect type is inputted into the kernel function k(x, x') and the value corresponding to the one defect type, and the difference between the output value of the discriminant function when the feature information of a training defect dataset of the other defect type is inputted into the kernel function k(x, x') and the value corresponding to the other defect type, decreases as the absolute value of either of the two differences decreases, and increases as the absolute value increases; and a regularization term multiplied by the regularization parameter, the regularization term has a positive correlation with the dimensional number of the discriminant function, and varies according to the weight of each feature constituting the feature information, and when the weight of each feature constituting the feature information which has been determined to minimize the value of the error function is temporarily adopted as the weight of each feature constituting the discriminant function, if the number of misclassification, which is the sum of the number of training defect dataset of the one defect type, for which the absolute value of the difference between the output value of the discriminant function when the feature information of the training defect dataset of the one defect type is inputted into the kernel function k(x, x') and the value corresponding to the other defect type is smaller than the absolute value of the difference between the output value of the discriminant function when the feature information of the training defect dataset of the one defect type is inputted into the kernel function k(x, x') and the value corresponding to the one defect type, and the number of training defect dataset of the other defect type for which the absolute value of the difference between the output value of the discriminant function when the feature information of the training defect dataset of the other defect type is inputted into the kernel function k(x, x') and the value corresponding to the one defect type is smaller than the absolute value of the difference between the output value of the discriminant function when the feature information of the training defect dataset of the other defect type is inputted into the kernel function k(x, x') and the value corresponding to the other defect type, is not less than a predetermined value; adjusts the regularization term parameter to determine the weight of each feature constituting the feature information again so as to minimize the value of the error function, and if the number of misclassification is less than the predetermined value; ascertains that the weight of each feature constituting the feature information which has been determined so as to minimize the value of the error function is adopted as the weight of each feature constituting the discriminant function to: the discriminant function.

The defect classification apparatus relating to the present invention performs mapping of a defect to be classified having an unknown defect type to a point in a mapping space having a higher-order dimension, and determine which of two regions of defect type, which are formed by separating the mapping space, contains the mapped point. Then, the defect classification apparatus relating to the present invention classifies that the defect type of a defect to be classified is the defect type corresponding to the region where the mapped point of the defect to be classified is located, out of the two regions of defect type. The defect classification apparatus relating to the present invention determines the discriminant function which indicates the decision boundary separating the mapping space in the following manner.

The defect classification apparatus relating to the present invention, first, determines the weight of each feature constituting feature information for a predetermined regularization parameter such that the value of an error function consisting of the sum of a classification error and a regularization term multiplied by the regularization parameter. Then, the defect classification apparatus relating to the present invention ascertains that if the number of misclassification when the weight of each feature constituting the feature information which is determined so as to minimize the value of the error function is temporarily adopted as the weight of each feature constituting the discriminant function is less than a predetermined value, the determined weight is adopted as the weight of each feature constituting the discriminant function to determine the discriminant function.

To decrease the value of the error function which consists of the sum of the classification error and the regularization term multiplied by the regularization parameter, it is necessary to decrease at least either one of the classification error and the regularization term. For example, when the regularization parameter is large, the effect of the regularization term on the value of the error function is dominant. The regularization term varies according to the weight of each feature constituting feature information. For this reason, when the regularization parameter is large, the weight to make the regularization term sufficiently small is determined as the weight to minimize the value of the error function. The dimensional number of the discriminant function and the regularization term have a positive correlation with each other. For this reason, the weight to make the regularization term sufficiently small is determined as the weight to minimize the value of the error function, and it is determined that the concerned weight is adopted as the weight of each feature constituting the discriminant function to determine the discriminant function so that excessive increase in the dimensional number of the discriminant function is suppressed and over-fitting (a phenomenon that a discriminant function which is excessively adapted to the feature information of a training defect dataset to be used to create a decision boundary (discriminant function) and the robustness for a defect to be classified having an unknown defect type is reduced. If over-fitting occurs when a training defect dataset whose feature has a singular value is present, a decision boundary (discriminant function) having an excessively high-order dimension is created such that the defect type is accurately judged even for a training defect dataset whose feature has a singular value) is suppressed. Therefore, the defect classification apparatus relating to the present invention can suppress over-fitting.

If the number of misclassification when the weight which is determined to minimize the value of the error function is temporarily adopted as the weight of each feature constituting the discriminant function is not less than a predetermined value, the defect classification apparatus relating to the present invention performs adjustment of regularization parameter to again determine the weight to minimize the value of the error function. If the regularization parameter is decreased as the result of the above described adjustment of the regularization parameter, while the effect of the regularization term on the value of the error function decreases, the effect of the classification error on the error function increases. Thus, adjustment to decrease the regularization parameter will result in that the weight to decrease the classification error becomes more able to be determined as the weight to minimize the value of the error function than before adjustment. The classification error is defined by the difference between the output value of the discriminant function when the feature information of a training defect dataset of one defect type is inputted into the kernel function k(x, x') (referred to as an "output value of the discriminant function corresponding to the one defect type") and the value corresponding to the one defect type, and the difference between the output value of the discriminant function when the feature information of a training defect dataset of the other defect type is inputted into the kernel function (x, x') (referred to as an "output value of the discriminant function corresponding to the other defect type") and the value corresponding to the other defect type. Further, the classification error decreases as either of the absolute values of the difference between the output value of the discriminant function corresponding to the one defect type and the value corresponding to the one defect type, and of the difference between the output value of the discriminant function corresponding to the other defect type and the value corresponding to the other defect type decreases, and increases as it increases. That is, if the classification error decreases, either the absolute value of the difference between the output value of the discriminant function corresponding to the one defect type and the value corresponding to the one defect type, or the absolute value of the difference between the output value of the discriminant function corresponding to the other defect type and the value corresponding to the other defect type decreases. If the absolute value of the difference between the output value of the discriminant function corresponding to one defect type and the value corresponding to the one defect type decreases, the number of training defect dataset of one defect type, for which the absolute value of the difference between the output value of the discriminant function corresponding to the one defect type and the value corresponding to the other defect type becomes larger than the concerned absolute value, decreases. Similarly, if the absolute value of the difference between the output value of the discriminant function corresponding to the other defect type and the value corresponding to the other defect type decreases, the number of training defect dataset of the other defect type, for which the absolute value of the difference between the output value of the discriminant function corresponding to the other defect type and the value corresponding to the one defect type becomes larger than the concerned absolute value, decreases. Therefore, as the classification error decreases, the number of misclassification decreases. Therefore, even if the number of misclassification when the weight determined before the adjustment of the regularization parameter is temporarily adopted as the weight of each feature constituting the discriminant function is not less than a predetermined value, by adjusting such that the regularization parameter decreases, it is possible to determine the weight for which the number of misclassification becomes less than a predetermined value, ascertain that the determined weight is adopted as the weight of each feature constituting the discriminant function, and determine the discriminant function.

As described so far, only when the weight, for which the number of misclassification when temporarily adopted as the weight of each feature constituting the discriminant function is less than the predetermined value, is determined out of the weight determined to minimize the value of the error function, the defect classification apparatus relating to the present invention ascertains that the determined weight is adopted as the weight of each feature constituting the discriminant function, and determines the discriminant function. Therefore, the defect classification apparatus relating to the present invention can accurately classify the defect type. However, as the regularization term increases, the possibility of over-fitting is increased. For this reason, for example, the regularization parameter is increased in initial stages, and when the weight by which the number of misclassification becomes less than the predetermined value cannot be determined, it is preferable to determine the weight for which the number of misclassification becomes less than the predetermined value by adjusting that the regularization parameter gradually decreases. Moreover, the above described classification error is set to be a value having a positive correlation with, for example, the sum of squares of the difference between the output value of the discriminant function corresponding to the one defect type and the value corresponding to the one defect type, and the difference between the output value of the discriminant function corresponding to the other defect type and the value corresponding to the other defect type. A value having a positive correlation with the above described sum of squares is set to be, for example, the square root of the above described sum of squares.

Moreover, the discriminant function consists of a kernel function k(x, x') and the weight of each feature, and has no mapping function. For this reason, there is no need of calculating a mapping function to determine the discriminant function. The computational complexity of calculating a mapping function is enormous. Therefore, the defect classification apparatus according to the present invention, which does not need to calculate a mapping function, can determine a discriminant function with a small computational complexity.

Moreover, the concept of "defect" in the present invention includes, besides cracks, a false mark such as a rubbing mark on the surface of the rolling product.

Furthermore, "the value corresponding to a defect type" in the present invention is a predetermined value so as to be able to classify one defect type from the other defect type, and is taken as different values for one and the other defect types.

Preferably, the defect classification apparatus is configured such that at least the extraction section thereof is placed in a rolling line of a rolling product, and the defect type of a defect to be classified, which occurs in the rolling product, is classified.

According to such a preferable configuration, since the defect type of a defect to be classified, which occurs in a rolling product, can be classified online, it is possible to quickly adjust the settings of a rolling mill in hot rolling lines (for example, a hot rolling line of wire rod and steel bar) and cold rolling lines in accordance with the defect classification information.

Meanwhile, a continuous hot rolling line generally consists of a rough rolling mill and a finish rolling mill, or a rough rolling mill, an intermediate rolling mill, and a finish rolling mill. While the above described defect classification apparatus having a preferable configuration can be placed between two rolling mill, in order to efficiently classify online the defect type of a defect to be classified, which occurs in a rolling product, it is most preferably placed on the downstream side (the downstream side in the rolling direction of rolling product) of a finish rolling mill.

Moreover, generally, a cooling apparatus for cooling the rolling product is installed in the downstream side of a finish rolling mill. When the above described defect classification apparatus of preferable configuration uses features extracted by performing image processing on a grabbed image sequence of a rolling product, the defect classification apparatus may be placed either on the upstream side (the upstream side in the rolling direction of rolling product) or the downstream side of the cooling apparatus. When placing the defect classification apparatus on the downstream side of the cooling apparatus, it is expected to accurately extract features of a defect to be classified in that the difference of brightness is more likely to increase between a defect region corresponding to the defect to be classified and the other region in a grabbed image sequence as the result of the rolling product being cooled. On the contrary to this, when placing the defect classification apparatus on the downstream side of the cooling apparatus, there is a risk that a false mark such as a rubbing mark on the surface of the rolling product appears in a grabbed image sequence as a result of contact between a guide, which is generally placed in the downstream side of the cooling apparatus, and the rolling product, leading to reduce the accuracy of classifying a crack from a false mark. In respect of reducing such risk, it is preferable to place the defect classification apparatus on the upstream side of the cooling apparatus. In reality, the location of placing the defect classification apparatus may be determined by the previous test for evaluating relative merits of the case in which the defect classification apparatus is placed on the upstream side of the cooling apparatus and the case of placing on the downstream side thereof.

Preferably, the defect classification apparatus is configured such that at least an image capture device for the rolling product as the extraction section is placed in the rolling line along with an eddy-current testing apparatus, and the defect type of a defect to be classified, which occurs in the rolling product, is classified by using features extracted by performing image processing on a grabbed image sequence of the rolling product which is grabbed by the image capture device.

According to such preferable configuration, the division of roles between an eddy-current testing apparatus (for example, a through-type differential eddy-current testing apparatus) which detects transverse defects and a defect classification apparatus which detects defects extending in the longitudinal direction of the rolling product (the two defect types to be classified by the defect classification apparatus are taken as defects extending in the longitudinal direction) can be conducted in the same rolling line, thereby improving the accuracy in classifying defects of the rolling product. Furthermore, similarly as described above, the defect classification apparatus of such preferable configuration may be placed either on the upstream side or the downstream side of the cooling apparatus when it is applied to the downstream side of the finish rolling mill of a hot rolling line.

According to the above described defect classification apparatus, it is possible to classify between cracks and false marks such as rubbing marks on the surface of the rolling product, which are difficult to be classified by a known classification method. That is, in the above described defect classification apparatus, the above described two defect types can be taken as a crack and a false mark such as a rubbing mark on the surface of the rolling product.

It is noted that even by using a known method, it is possible to classify between a defect in which cracks and false marks are mixed in the rolling product and a healthy area of the rolling product. For example, it is possible to exclude the region corresponding to the above described healthy area thereby extracting the region corresponding to the above described defect by performing known image processing on a grabbed image sequence of the rolling product. Therefore, by applying the above described defect classification apparatus only to the defects classified (extracted) by the known classification method, it is possible to classify between cracks and false marks with efficiency.

Furthermore, the feature used in the defect classification apparatus relating to the present invention will not be particularly limited. For example, the defect classification apparatus relating to the present invention, in which the extraction section comprises at least one of an image capture device for the rolling roll, an eddy-current testing apparatus for performing eddy-current testing on the rolling product, and an ultrasonic testing apparatus for performing ultrasonic testing on the rolling product, can classify the defect type of a defect to be classified which occurs in the rolling product by using at least one kind of features among the features extracted by performing image processing on a grabbed image sequence of the rolling product grabbed by the image capture device, the features extracted by performing eddy-current testing on the rolling product with the eddy-current testing apparatus, and the features extracted by performing ultrasonic testing on the rolling product with the ultrasonic testing apparatus.

Advantageous Effects of Invention

The present invention can provide a defect classification apparatus which suppresses over-fitting and accurately classifies the defect type of a defect.

BRIEF DESCRIPTION OF DRAWINGS

FIG. 2 is a schematic view showing information relating to a training defect dataset.

DESCRIPTION OF EMBODIMENTS

Hereafter, referring to the appended drawings, an embodiment of the present invention will be described by taking an example of a case where an object in which a defect to be classified occurs is a wire rod which is a rolling product, and features extracted by performing image processing on a grabbed image sequence of the wire rod are used. Note that in each formula described herein, a parameter shown in bold italics means a vector.

Figure 1A:
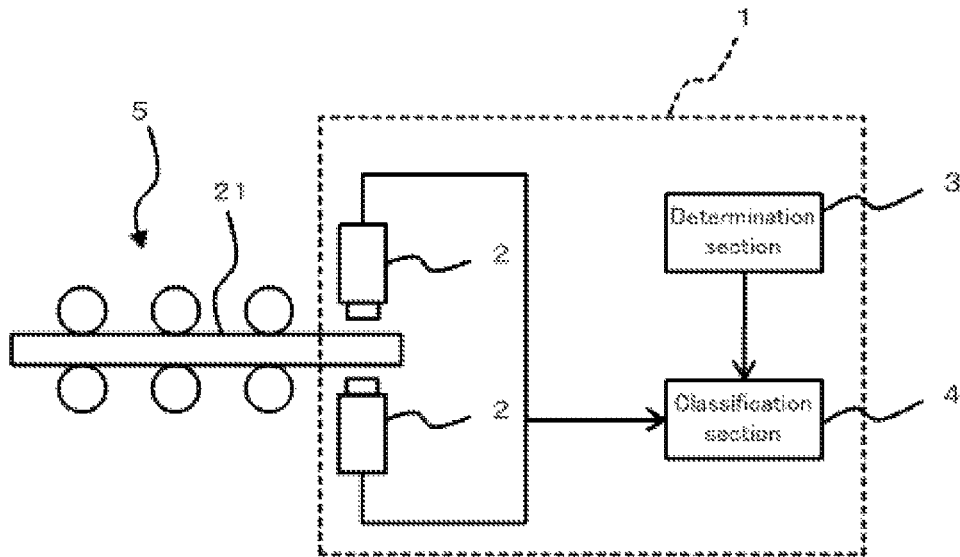
FIG. 1 (FIGS. 1A and 1B) is a schematic configuration drawing of a defect classification apparatus relating to an embodiment of the present invention.

FIG. 1A is a schematic configuration drawing showing an example of a defect classification apparatus 1 of the present embodiment. As shown in FIG. 1A, the defect classification apparatus 1 includes an image capture device (a camera 2 and a light source (not shown)) as an extraction section for extracting features, a determination section 3, and a classification section 4. The camera 2 is placed at a plurality of (for example, four) points along the circumferential direction of a wire rod 21 transported along a hot rolling line, to grab an image sequence of the wire rod 21. Further, a light source (not shown) for illuminating the wire rod 21 is placed in the surrounding of the camera 2. The camera 2 and the light source are placed on the downstream side (the downstream side in the rolling direction (transporting direction) of the wire rod 21) of the finish rolling mill 5 which is installed in the hot rolling line.

Figure 1B:
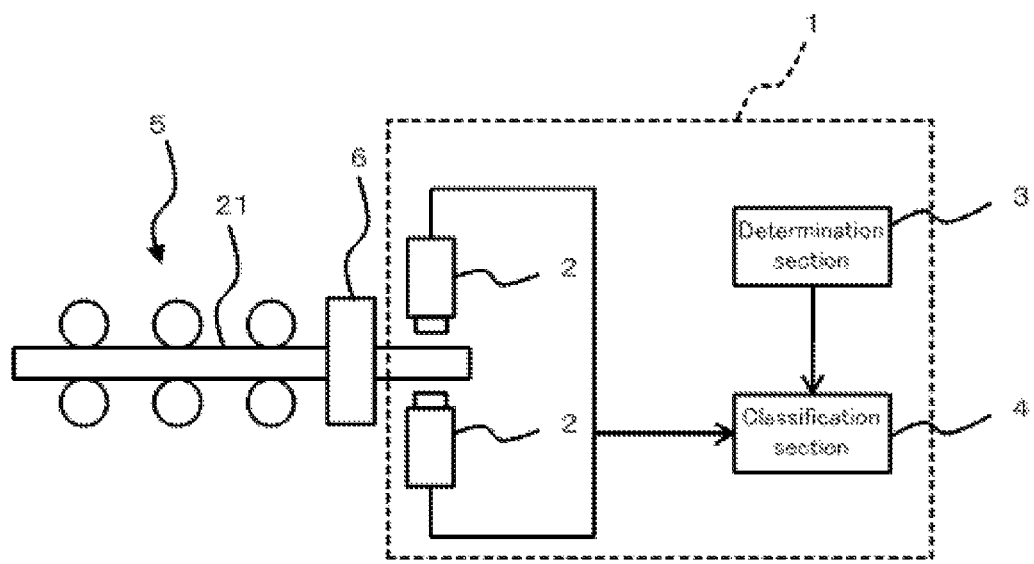

FIG. 1B is a schematic configuration drawing showing another example of the defect classification apparatus 1 of the present embodiment. The example shown in FIG. 1B is different from the example shown in FIG. 1A in that a through-type differential eddy-current testing apparatus 6 is placed on the downstream side of the finish rolling mill 5, and the camera 2 and the light source are placed on the downstream side of the eddy-current testing apparatus 6.

The determination section 3 determines a discriminant function which indicates a decision boundary for classifying the defect type of a defect to be classified having an unknown defect type. This decision boundary separates a mapping space, which has a dimensional number higher than the number of features constituting feature information (a vector), whose components include a plurality of features indicating the attributes of a defect to be classified, into regions of two defect types (hereafter, one of the two defect types is referred to as "defect type A" and the other defect type as "defect type B"). Defect type A and defect type B are mutually different defect types specified in priori by a user etc. of the defect classification apparatus 1. Defect type A and defect type B may be defect types of which levels of severity (the levels of effect on the quality of the wire rod 21) is different from each other. Moreover, defect type A and defect type B may be for example defect types in which the causes for occurrence are mutually different.

As the feature, it is possible to use the size, area, brightness, and others of a defect region corresponding to a defect, which is extracted by performing image processing on a grabbed image sequence which is grabbed by the camera 2. The number of features constituting feature information is not limited, provided it is a plural number.

The determination section 3 determines a discriminant function by using the feature information of a training defect dataset whose defect type is known as either defect type A or defect type B. The feature information of a training defect dataset, which is to be inputted to the determination section 3, is extracted, for example, by using the image processing function of the classification section 4 to be described later. That is, a grabbed image sequence of a training defect dataset which has been grabbed by the camera 2, is inputted to the classification section 4, and image processing is performed in the classification section 4 to obtain feature information of the training defect dataset. Then, the resulting feature information of the training defect dataset is inputted to the determination section 3. Alternatively, if supposed that the determination section 3 itself has an image processing function, it is also possible to obtain the feature information of a training defect dataset by inputting a grabbed image sequence of the training defect dataset grabbed by the camera 2 into the determination section 3 and performing image proceeding in the determination section 3. The feature information of a training defect dataset of defect type A, the feature information of a training defect dataset of defect type B, and the above described feature information of a defect to be classified consist of the same kind of features. A training defect dataset is a defect whose defect type is known (the defect type thereof has been labeled by a user). As shown in FIG. 2, each feature constituting the feature information of each training defect dataset of defect type A, and each feature constituting the feature information of each training defect dataset of defect type B are tied to an identifier of a training defect dataset, and the defect type of a training defect dataset and stored in the determination section 3. Further, as shown in FIG. 2, the value of each feature constituting the feature information of each training defect dataset is normalized so as to be a value within a range of 0 to 1.

The discriminant function f(x) to be determined by the determination section 3 is represented by the following Formula (1).

$$f(x) = w^T \phi(x) \quad (1)$$

Where, w indicates weight factor (a vector) whose components each include the weight of each feature constituting the feature information. The character x described in Formula (1) indicates the feature information (a vector) of a training defect dataset of defect type A or defect type B. $\phi(\bullet)$ is a mapping function for mapping a data point (a point at the tip of a vector) indicating feature information into the mapping space, and having a positive definiteness. Examples of the mapping function having a positive definiteness include a function of Gaussian distribution.

The computational complexity of the mapping function $\phi(\bullet)$ is enormous. To make it possible to determine the discriminant function f(x) with a small computational complexity, the present embodiment uses the discriminant function f(x) represented by the following Formula (2). In the following description, the discriminant function f(x) means a discriminant function f(x) represented by the following Formula (2).

$$f(x) = \Sigma \alpha k(x, x') \quad (2)$$

Where, $\alpha$ indicates the weight of each feature constituting feature information. k(x, x') indicates a kernel function in which a matrix K whose elements are given as k(x, x') is positive semi-definite. The character x described in or after Formula (2) indicates feature information (a vector) of a training defect dataset of defect type A. The character x' indicates feature information (a vector) of a training defect dataset of defect type B. The matrix K whose elements are given as k(x, x') is a matrix whose elements include output values of a kernel function which are obtained when the feature information x of a training defect dataset of defect type A is inputted into the kernel function k(x, x'), and output values of the kernel function which are obtained when the feature information x' of a training defect dataset of defect type B is inputted into the kernel function k(x, x').

Examples of the kernel function k(x, x') where matrix K whose elements are given as the kernel function k(x, x') is positive semi-definite include the following five kernel functions (x, x').

$$k(x, x') = f(x)k_1(x, x')f(x')$$

$$k(x, x') = q(k_1(x, x'))$$

$$k(x, x') = \exp(k_1(x, x'))$$

$$k(x, x') = x^T K x'$$

$$k(x, x') = k_a(x_a + x_a') + k_a(x_b + x_b')$$

Moreover, other examples of the kernel function k(x, x') in which the matrix K whose elements are given as the kernel function k(x, x') is positive semi-definite include the sigmoid function and the Gauss function described in the following formulas.

$$\text{Sigmoid function: } k(x, x') = \frac{1}{1 + \exp(-\beta x \cdot x')}$$

$$\text{Gauss function: } k(x, x') = \exp\left(\frac{-\|x - x'\|^2}{2\sigma^2}\right)$$

It is noted that in the above described exemplary seven kernel functions k(x, x'), $f(\bullet)$ indicates an arbitrary function, $q(\bullet)$ indicates a polynomial having non-negative coefficients, $k_1(\bullet, \bullet)$, $k_a(\bullet, \bullet)$, and $k_b(\bullet, \bullet)$ indicate arbitrary kernel functions, subscripts a and b indicate identifiers of training defect dataset, β indicates a gain of the sigmoid function, and σ indicates variance.

Formula (2) is derived as described below.

$$k(x, x') = \phi(x)^T \phi(x') = \sum_{m=1}^{d} \phi_m(x)\phi_m(x') \quad (3)$$

Defining k(x, x') as described above, the following Formula (4) will be derived.

$$k(x, x') = \sum_{m=1}^{d} x^m (x')^m \quad (4)$$

The character d indicates the number of features constituting feature information. When the number of features constituting feature information is made to be sufficiently large, the following Formula (5) will be derived from Formula (1).

$$f(x) = \sum \alpha k(x, x') \quad (5)$$
$$= \sum \alpha \phi(x)^T \phi(x')$$

Where, the weight factor w is represented by the following Formula (6).

$$w \Sigma \alpha \phi(x) \quad (6)$$

According to the definition (Formula (3)) of the kernel function k(x, x'), Formula (2) is derived from Formula (1) by using Formula (6). The discriminant function f(x) of Formula (2) is a function whose dimensional number is affected by the number of features constituting feature information of a training defect dataset.

Hereafter, the procedure to determine the discriminant function f(x) will be described appropriately referring to FIG. 3. The determination section 3 first classify whether or not the number of misclassification is less than a predetermined value (step S1 of FIG. 3). The number of misclassification is the sum of: the number of training defect dataset of defect type A, for which the absolute value of the difference between the output value of the discriminant function f(x) when the feature information x of a training defect dataset of defect type A is inputted into the kernel function k(x, x') of the discriminant function f(x) (hereafter, referred to as an "output value of the discriminant function corresponding to defect type A") and the value corresponding to defect type B is smaller than the absolute value of the difference between the output value of the discriminant function corresponding to defect type A and the value corresponding to defect type A; and the number of training defect dataset of defect type B, for which the absolute value of the difference between the output value of the discriminant function f(x) when the feature information x' of a training defect dataset of defect type B is inputted into the kernel function k(x, x') of the discriminant function f(x) (hereafter, referred to as an "output value of the discriminant function corresponding to defect type B") and the value corresponding to defect type A is smaller than the absolute value of the difference between the output value of the discriminant function corresponding to defect type B and the value corresponding to defect type B. Moreover, upon input of the feature information x of the training defect dataset of defect type A, or the feature information x' of the training defect dataset of defect type B into the kernel function k(x, x') of the discriminant function f(x), the weight α of each feature constituting the feature information of the discriminant function f(x) is taken as an arbitrary value (for example 1). Furthermore, in the present embodiment, it is assumed that the value corresponding to defect type A is 1, and the value corresponding to defect type B is −1. The values corresponding to defect type A and defect type B are predetermined by the user of the defect classification apparatus 1 to be different values from each other such that defect type A and defect type B are identical.

Figure 3:
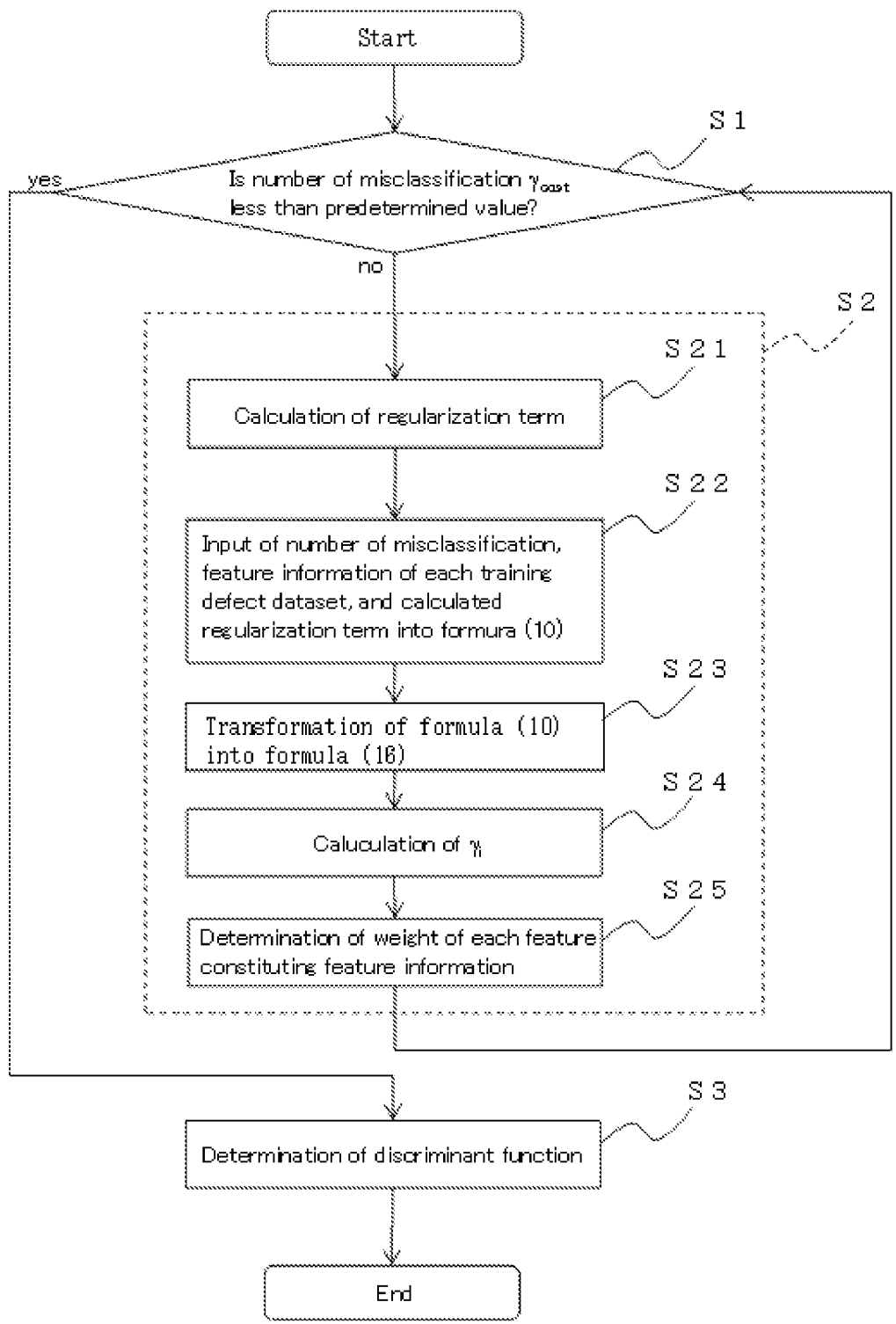
FIG. 3 is a flowchart showing the procedure to determine a discriminant function.

When it is classified that the number of misclassification is not less than a predetermined value, the determination section 3 determines the weight α of each feature constituting feature information, which minimizes the value of error function that consists of the sum of the classification error and the regularization term $\alpha^T K \alpha$ multiplied by a regularization parameter λ (step S2 of FIG. 3). The minimum value of the error function is represented by the following Formula (7).

$$\min_{\alpha} \sum_{i=1}^{n} \gamma_{cost}(y^{(i)} f(x^{(i)})) + \lambda \alpha^t k \alpha \quad (7)$$

Where, super script (i) indicates an identifier of a training defect dataset. Note that the regularization parameter λ takes on a value within a range of 0 to 1. The classification error, which is defined by the difference between the output value of the discriminant function f(x) when the feature information of a training defect dataset of defect type A is inputted into the kernel function k(x, x') and the value corresponding to defect type A, and the difference between the output value of the discriminant function f(x) when the feature information of a training defect dataset of defect type B is inputted into the kernel function k(x, x') and the value corresponding to defect type B, decreases as the absolute value of either of the two differences decreases, and increases as the absolute value increases.

The term $\gamma_{cost}$ of Formula (7) is represented by the following Formula (8).

$$\gamma_{cost} = max\{0, 1 - yf(x)\} \quad (8)$$

Formula (8) is a convex function which approximates the following Formula (9).

$$\gamma(f(x), y) = \frac{1}{2}(y - \text{sgn}[f(x)])^2 \quad (9)$$
$$= 1 - y\text{sgn}[f(x)]$$
$$= 1 - \text{sgn}[yf(x)]$$

The term y of Formula (9) indicates a vector whose components are weights of each feature. When the feature information of a training defect dataset of defect type A is inputted into the kernel function k(x, x') to find the classification error, each component of vector y is taken as 1, and when the feature information of a training defect dataset of defect type B is inputted into the kernel function k(x, x'), each component of vector y is taken as −1. The term sgn[f(x)] in Formula (9) is represented by the following Formula (10).

$$\text{sgn}[f(x)] = \begin{cases} 1 (f(x) \geq 0) \\ -1 (f(x) < 0) \end{cases} \quad (10)$$

The regularization term $\alpha^T K\alpha$ is represented by the following Formula (11).

$$\|w\|^2 = \sum_{i=1}^{n}\sum_{j=1}^{n}\alpha_i\alpha_j\phi(x^{(i)})^T\phi(x^{(j)}) \quad (11)$$
$$= \alpha^T K\alpha$$

Where, the subscript i indicates an identifier to represent the type of the feature constituting the feature information of a training defect dataset of defect type A. The subscript j indicates an identifier to represent the type of the feature constituting the feature information of a training defect dataset of defect type B.

It is seen from Formula (11) that the regularization term $\alpha^T K\alpha$ has a positive correlation with the weight $\alpha$ of each feature. The regularization term $\alpha^T K\alpha$ is derived as follows. A linear sum $w_0$ of each feature of a training defect dataset of defect type A is represented by the following Formula (12).

$$w_0 = \sum_i \alpha_i \phi(x^{(i)}) \quad (12)$$

Moreover, since the weight factor w is the sum of the linear sum $w_0$ and a $\xi$ component orthogonal to a mapped point $\phi(x^{(i)})$ which is mapping of a data point indicating the feature information of a training defect dataset, it is represented by the following Formula (13).

$$w = w_0 + \xi \quad (13)$$

Where, from the condition that the inner product $\phi(x^{(j)})^T \cdot \xi$ between the weight factor w and the mapped point $\phi(x^{(j)})$ is 0, f(x) of Formula (5) is represented by the following Formula (14).

$$f(x^{(j)}) = w^T\phi(x^{(j)}) = w_0^T\phi(x^{(j)}) \quad (14)$$

Thus, it is seen that the term $\gamma_{cost}$ of the left-hand side of Formula (8) is not dependent on the value of the $\xi$ component. Moreover, the following Formula (15) can be derived from the orthogonality between the linear sum $w_0$ and the $\xi$ component.

$$\lambda\|w\|^2 = \lambda(\|w_0\|^2 + \|\xi\|^2) \quad (15)$$

From Formula (15), it is obvious that $\lambda\|w\|^2$ becomes a minimum value when $\xi=0$. Therefore, it is when $w=w_0$ that the error function becomes minimum. Here, utilizing Formula (12) allows the derivation of Formula (11) from Formula (15).

From Formulas (11) and (2), the regularization term $\alpha^T K\alpha$ has a positive correlation with the dimensional number of the discriminant function f(x) of Formula (2).

Hereafter, details of the procedure to determine the weight $\alpha$ of each feature constituting the feature information that minimizes the value of the error function (step S2 of FIG. 3) will be described. First, the determination section 3 inputs an arbitrary value (for example, 1) into the weight $\alpha_i$ and the weight $\alpha_j$ of Formula (11), inputs feature information of a training defect dataset of defect type A into $x^{(i)}$ of Formula (11), and inputs feature information of a training defect dataset of defect type B into $x^{(j)}$ to calculate the regularization term $\alpha^T K\alpha$ (step S21 of FIG. 3).

Next, $\gamma_{cost}$ of the left-hand side of Formula (8) is inputted into $y^{(i)}$ of Formula (7), the feature information of each training defect dataset of defect type A or defect type B is inputted into $x^{(i)}$ of Formula (7), and the value of the regularization term $\alpha^T K\alpha$ calculated in step S21 is inputted into the regularization term $\alpha^T K\alpha$ of Formula (7) (step S22 of FIG. 3). It is noted that, in this occasion, the regularization parameter of Formula (7) is an initial value and, here, the initial value is taken as 1.

Next, Formula (7) is transformed into the following Formula (16) (step S23 of FIG. 3).

$$\min_{\alpha} \sum_{i=1}^{n} \xi_i + \frac{\lambda}{2}\alpha^T K\alpha \quad (16)$$

The transformation from Formula (7) to the following Formula (16) will be described. Letting the output of the classification error for the feature information $x^{(i)}$ and the value $y^{(i)}$ be $\xi_i$, the minimum value of the output $\xi_i$ will be the minimum value defined by two inequalities (17) and (18).

$$\xi_i \geq 0 \quad (17)$$

$$\xi_i \geq 1 - y^{(i)}f(x^{(i)}) = 1 - y^{(i)}\sum_{j=1}^{n}\alpha_j K_{ij} = 0 \quad (18)$$

$$K_{ij} = k(x^{(i)}, x^{(j)})$$

The output $\xi_i$ when it becomes a minimum value is called as a slack variable, and Formula (7) is transformed into Formula (16) with Formulas (17) and (18) as constraints by introducing the output $\xi_i$ when it becomes a minimum value into Formula (7).

Formula (16) takes on a form of a convex quadratic programming problem relating to the output $\xi$ and the weight $\alpha$ of each feature constituting the feature information. Hereafter, the solution of the convex quadratic programming problem of Formula (16) will be shown.

Formula (16) is solved by using the Lagrange undefined multiplier method. The following Formula (19) is defined as Lagrangian. Definition region: $\Omega \subseteq R^n$ Where, Rn indicates the entire real numbers.
Constraints: $g_i(w) \leq 0$, $h_i(w) = 0$
Note that $g_i(w)$ and $h_i(w)$ indicate arbitrary functions.
Convex quadratic programming problem:

$$\min f(w), w \in \Omega \quad (19)$$

$$L(w, \alpha, \beta) = f(w) + \sum_{i=1}^{k}\alpha_i g_i(w) + \sum_{i=1}^{m}\beta_i h_i(w)$$

$$= f(w) + \alpha'_g(w) + \beta'_h(w)$$

A necessary and sufficient condition to solve the following convex quadratic programming problem using Lagrangian $L(w, \alpha, \beta)$ is from the KKT (Karush-kuhn-Tucker) condition that $\alpha^*$ and $\beta^*$ that satisfy the following Formulas (20) to (24) exist.
Convex quadratic programming problem
Definition region: $\Omega \subseteq R^n$
Constraints: $g_i(w) \leq 0$, $h_i(w) = 0$
Note that $g_i(w)$ and $h_i(w)$ indicate affine functions.

Convex quadratic programming problem:

$$\min f(w), w \in \Omega \qquad (20)$$

$$\frac{\delta L(w^*, \alpha^*, \beta^*)}{\delta w} = 0$$

$$\frac{\delta L(w^*, \alpha^*, \beta^*)}{\delta \beta} = 0 \qquad (21)$$

$$\alpha_i * g_i(w^*) = 0 \qquad (22)$$

$$g_i(w^*) \leq 0 \qquad (23)$$

$$\alpha_i * \geq 0 \qquad (24)$$

Where, $\alpha$ and $\beta$ indicate Lagrange multipliers in Formulas (19) to (24). The character $w^*$ indicates the weight factor when it is optimized. $\alpha^*$ and $\beta^*$ indicate Lagrange multipliers $\alpha$ and $\beta$ when $w^*$ is obtained.

The following Formula (25) can be derived from Formula (16) using Formula (19).

$$L(\xi, \alpha, \beta, \beta, \gamma) = \qquad (25)$$

$$\sum_{i=1}^{n} \xi_i + \frac{\lambda}{2} \alpha^T K \alpha - \sum_{i=1}^{n} \beta_i \xi_i - \sum_{i=1}^{n} \gamma_i \left( \xi_i - 1 + y^{(i)} \sum_{j=1}^{n} \alpha_j K_{ij} \right)$$

Constraints: $\beta_i \geq 0$, $\gamma_i \geq 0$

Where, $\gamma$ indicates a Lagrange multiplier.

If it is supposed that the feasible region in which an optimal solution is sought is not $\phi$ (empty set) in a general convex quadratic programming problem to minimize an objective function which is a convex function represented by the following Formula (26), the following Formula (26) is transformed into the following Formula (27).

Objective function:

$$\frac{1}{2} w^T Q w - k^T w \qquad (26)$$

Constraint: $Xw \leq c$

In from Formula (26) to the following Formula (29), Q indicates an n×n positive definite matrix, k indicates an n-vector, c indicates an m-vector, w indicates a vector to be optimized, and X indicates an m×n matrix.

$$\max_{\alpha \geq 0} \left( \min_w \left( \frac{1}{2} w^T Q w - k^T w + \alpha^T (Xw - c) \right) \right) \qquad (27)$$

Here, the problem to determine the minimum value of w in Formula (27) constitutes an unconstrained optimization problem, and the optimal solution is represented by the following Formula (28).

$$w = Q^{-1}(k - X^T \alpha) \qquad (28)$$

Substituting the right-hand side of Formula (28) into the vector w to be optimized in Formula (26) will result in a dual problem to maximize the objective function represented by the following Formula (29) under the following constraint.

Objective function:

$$-\frac{1}{2} \alpha^T P \alpha - \alpha^T d - \frac{1}{2} k^T Q k \qquad (29)$$

Constraint: $\alpha \geq 0$ $$(P = XQ^{-1}X^T, d = c - XQ^{-1}k)$$

Thus, the quadratic programming problem can be transformed into a dual problem with simpler constraints. By taking advantage of this property, it is possible to significantly reduce the computational complexity of the search of an optimal solution.

Similarly with the above described procedure, the quadratic programming problem represented by Formula (25) is led to a dual problem. First, Lagrangian L ($\xi$, $\alpha$, $\beta$, $\gamma$) with which Formula (25) is differentiated with respect to the weight $\alpha_i$ and the output $\xi_i$ is set to be 0 (see the following Formula (30)).

$$\frac{\delta L(\xi, \alpha, \beta, \gamma)}{\delta \alpha_i} = \sum_{i=1}^{n} (\lambda K_{ij} \alpha_j - \gamma_i y^{(j)} K_{ij}) = 0 \qquad (30)$$

Where, since K is a symmetric matrix, $K^T = K$, and therefore the following Formula (31) can be derived from Formula (30).

$$\lambda K \alpha - K \hat{\gamma} = 0 \qquad (31)$$

Where $\hat{\gamma} = (\hat{\gamma}_1, \hat{\gamma}_2, \ldots, \hat{\gamma}_n)$, $\hat{\gamma}_1 = \gamma_1 y^{(i)}$, $i = 1, \ldots, n$ (32)

If it is supposed that the matrix K is positive definite, the following Formula (33) can be obtained.

$$\alpha_i = \frac{1}{\lambda} \gamma_i y^{(i)} \qquad (33)$$

When the following Formula (34) is satisfied, the output $\xi_i$ can be made as small as desired. That is, since the Lagrange function (see Formula (25)) of a dual problem becomes $-\infty$, when considering a dual problem, it is sufficient to take into account only a case in which the constraints of the following Formula (35) is included.

$$1 - \beta_i - \gamma_i \neq 0 \qquad (34)$$

$$1 - \beta_i - \gamma_i = 0 \qquad (35)$$

In this way, since the coefficient of a variable is 0 in a Lagrange function which is represented by a first order expression, the dual problem is irrelevant to the output $\xi_i$. Therefore, the weight $\alpha_i$ is substituted by Formula (33) to maximize the Lagrange function of the following Formula (36) under the constraint of Formula (35).

$$L_{dp}(\beta, \gamma) = \sum_{i=1}^{n} \gamma_i - \frac{1}{2\lambda} \sum_{i=1}^{n} \sum_{j=1}^{n} y^{(i)} y^{(j)} \gamma_i \gamma_j K_{ij} \qquad (36)$$

Moreover, from the conditions $\beta_i \geq 0$ and $\gamma_i \geq 0$, the constraint of Formula (35) becomes as the following Formula (37).

$$0 \leq \gamma_i \leq 1 \qquad (37)$$

Calculating $\gamma_i$ from Formula (36) (step S24 of FIG. 3) by using a known optimization method such as a steepest descent method and an interior point method and substituting the calculated $\gamma_i$ into Formula (33) allows the determination of the weight α of each feature constituting feature information to minimize the error function (step S25 of FIG. 3).

The determination section 3 temporarily adopts the weight α of each feature constituting the feature information of a training defect dataset, which is determined as described above, as the weight α of each feature constituting the feature information of training defect dataset of the discriminant function f(x). Then, in a similar manner as in step S1 of FIG. 3, the determination section 3 calculates the number of misclassification when the determined weight α of each feature is temporarily adopted as the weight α of each feature constituting the discriminant function f(x). If the calculated number of misclassification is not less than a predetermined value, the determination section 3 makes adjustment that the regularization parameter λ becomes smaller, and determines again the weight α of each feature constituting the feature information to minimize the error function as described above (step S2 of FIG. 3). Moreover, in the calculation of the regularization term in step S21 after the adjustment that the regularization parameter λ becomes smaller, the weight α of each feature determined in the previous step S25 is inputted into the weight $α_i$ and the weight $α_j$ of Formula (11). On the other hand, if the calculated number of misclassification is less than the predetermined value, it is ascertained that the determined weight α of each feature is adopted as the weight α of each feature constituting the discriminant function f(x), and the discriminant function f(x) is determined (step S3 of FIG. 3).

The determination section 3 of the present embodiment, as described above, sets the initial value of the regularization parameter λ to be the maximum value of the regularization parameter λ, and makes adjustment such that if the number of misclassification is less than the predetermined value, the regularization parameter λ is made smaller. When the regularization parameter λ is large, the effect of the regularization term $α^T K α$ on the value of the error function is large. For this reason, when the regularization parameter λ is large, the weight α of each feature which makes the regularization term $α^T K α$ to be sufficiently small is determined as the weight α of each feature which minimizes the value of the error function. The dimensional number of the discriminant function f(x) and the regularization term $α^T K α$ have a positive correlation. For this reason, if the weight α of each feature which makes the regularization term $α^T K α$ to be sufficiently small is determined as the weight α of each feature that minimizes the value of the error function, and it is ascertained that the weight α of each feature is adopted as the weight α of each feature constituting the discriminant function f(x) and the discriminant function is determined, it is possible to suppress the increase in the dimensional number of the discriminant function (decision boundary), thereby allowing the suppression of over-fitting. Further, even when the weight α of each feature which makes the regularization term to be sufficiently small is determined, when the number of misclassification when the weight α of each feature is temporarily adopted as the weight α of each feature constituting the discriminant function f(x), it will not be ascertained that the weight α of each feature is adopted as the weight α of each feature constituting the discriminant function f(x). In this case, adjustment is made such that the regularization parameter λ becomes smaller, and the weight α of each feature to minimize the value of the error function is determined again. Making the regularization parameter λ smaller will result in that the effect of the regularization term $α^T K α$ on the value of the error function will decrease, while the effect of the classification error on the value of the error function will increase. For this reason, if adjustment is made such that the regularization parameter λ becomes smaller, it becomes more possible than before the adjustment that the weight α of each feature that decreases the classification error is determined as the weight α of each feature that minimizes the value of the error function. The classification error is specified as the difference between the output value of the discriminant function corresponding to defect type A and the value corresponding to defect type A, and the difference between the output value of the discriminant function corresponding to defect type B and the value corresponding to defect type B. Further, the classification error decreases as the absolute value of either of the difference between the output value of the discriminant function corresponding to defect type A and the value corresponding to defect type A, and the difference between the output value of the discriminant function corresponding to defect type B and the value corresponding to defect type B decreases, and increases as either of them increases. That is, as the classification error decreases, either the absolute value of the difference between the output value of the discriminant function corresponding to defect type A and the value corresponding to defect type A, or the absolute value of the difference between the output value of the discriminant function corresponding to defect type B and the value corresponding to defect type B decreases. As the absolute value of the difference between the output value of the discriminant function corresponding to defect type A and the value corresponding to defect type A decreases, the number of training defect dataset of defect type A, in which the absolute value of the difference between the output value of the discriminant function corresponding to defect type A and the value corresponding to defect type B becomes larger than the foregoing absolute value, decreases. Similarly, as the difference between the output value of the discriminant function corresponding to defect type B and the value corresponding to defect type B decreases, the number of training defect dataset of defect type B, in which the absolute value of the difference between the output value of the discriminant function corresponding to defect type B and the value corresponding to defect type B becomes larger than the foregoing absolute value, decreases. Therefore, as the classification error decreases, the number of misclassification decreases. Thus, even when the number of misclassification when the weight α of each feature determined before the adjustment of the regularization parameter is temporarily adopted as the weight α of each feature constituting the discriminant function f(x) is not less than the predetermined value, it is possible to determine the weight α of each feature for which the number of misclassification becomes less than the predetermined value by making adjustment that the regularization parameter λ is decreased, and to ascertain that the determined weight α of each feature is adopted as the weight α of each feature constituting the discriminant function, thereby determining the discriminant function f(x).

Moreover, the discriminant function f(x) represented by Formula (2) has a kernel function k(x, x') and a weight α for each feature constituting feature information, and does not have a mapping function. For this reason, when calculating the number of misclassification, there is no need of calculating the mapping function. In other words, there is no need of calculating a mapping function to determine a discriminant function. The computational complexity of a mapping function is enormous. For this reason, the defect classification apparatus 1, which does not need to calculate a mapping function to determine the discriminant function f(x), can determine the discriminant function f(x) with a small computational complexity.

The classification section 4 classifies whether the defect type of a defect to be classified, which has occurred in a wire rod 21 of which image sequence has been grabbed by a camera 2, belongs to defect type A or defect type B. The classification section 4, which has an image processing function, determines a defect region corresponding to a defect to be classified in a wire rod 21 from a grabbed image sequence of the wire rod 21 grabbed by the camera 2 by means of a known image processing method and calculates the feature of the defect to be classified. The classification section 4 inputs the feature information consisting of calculated features into the kernel function k(x, x') of the discriminant function f(x) determined by the determination section 3, and calculates an output value of the discriminant function f(x), that is, a mapped point which is mapping of a data point indicating the concerned feature information to a mapping space. Then, the classification section 4 classifies that the defect type of a defect to be classified is the defect type corresponding to either of the above describe two regions, wherein the mapped point is located. To be specific, the classification section 4 compares the absolute value of the difference between the output value of the discriminant function f(x) when the feature information of a defect to be classified is inputted and the value corresponding to defect type A, with the absolute value of the difference between the output value of the discriminant function f(x) and the value corresponding to defect type B, and if the former is smaller, classifies that the defect to be classified belongs to defect type A, and if the latter is smaller, that the defect to be classified belongs to defect type B. In the present embodiment, since as described above, the value corresponding to defect type A is taken as 1, and the value corresponding to defect type B is taken as −1, the condition when the discriminant function f(x) takes a middle value between the both, that is, f(x)=0 corresponds to the decision boundary to separate the above described mapping space.

Further, the weight of feature that has little or no effect on the output value of the discriminant function f(x) is highly likely to be determined to be 0 by the determination section 3. As described above, the determination section 3 determines the weight α of each feature constituting the feature information that minimizes the error function. The error function is a function that consists of the sum of the classification error and the regularization term $\alpha^T K \alpha$. The classification error, which is defined by the difference between the output value of the discriminant function corresponding to defect type A and the value corresponding to defect type A, and the difference between the output value of the discriminant function corresponding to defect type B and the value corresponding to defect type B, decreases as the absolute value of either of the two differences decreases, and increases as it increases. That is, the classification error varies according to the output value of the discriminant function f(x). The discriminant function f(x) varies according to the weight of feature from Formula (2). For this reason, the variation in the classification error is small when the weight of feature that has little or no effect on the output value of the discriminant function f(x) is varied. The regularization term $\alpha^T K \alpha$ has a positive correlation with the weight α of each feature. For this reason, the value of the error function consisting of the sum of the classification error and the regularization term is highly likely to decrease as the result of making the weight of feature, for which the variation of classification error is small to be a minimum (that is, 0). Thus, the weight of the feature that has little or no effect on the output value of the discriminant function f(x) is highly likely to be determined to be 0 by the determination section 3.

The feature information that is inputted into the kernel function k(x, x') of the discriminant function f(x) determined by the determination section 3 in order for the classification section 4 to classify the defect type of a defect to be classified may be substituted with feature information which consists of features other than those for which the weights are determined to be 0. When such feature information is taken as the feature information to be inputted into the kernel function k(x, x') of the discriminant function f(x) determined by the determination section 3, the feature whose weight is determined to be 0 will not be inputted into the kernel function k(x, x') of the discriminant function f(x), and for that part, the computational complexity for the classification of the defect type of a defect to be classified will be reduced. Such reduction in the computational complexity for the classification of the defect type of a defect to be classified allows rapid classification of the defect type of a defect to be classified. Further, as described above, the weight of the feature that has little or no effect on the output value of the discriminant function f(x) is highly likely to be determined to be 0. Thus, even if a feature whose weight has been determined to be 0 is not inputted into the kernel function k(x, x') of the discriminant function f(x), it is possible to perform the classification of the defect type of a defect to be classified by use of the output value of the discriminant function f(x) at a certain level of accuracy or above.

In what has been described so far, although description has been made on the classification of a defect which has occurred in a wire rod by the defect classification apparatus 1, the defect to be classified by the defect classification apparatus 1 is not limited to those which have occurred in a wire rod, but may be those which occurs in a rolling product, for example, a tube, a sheet material, etc.

Further, in the present embodiment, the classification error is represented by $\gamma_{cost}$ of Formula (8) which is a convex function. Since $\gamma_{cost}$ of Formula (8) is a convex function, it is possible to find the weight α to minimize the value of classification error without falling into a local solution. For this reason, it is possible to effectively determine the weight α to make the classification error to be less than the predetermined value.

Further, although in the present embodiment, description has been made on an example in which classification is made on to which of the two defect types (defect type A and defect type B) the defect type of a defect to be classified belongs, it is also possible to classify to which of three or more defect types the defect type of a defect to be classified belongs by repeating the above described operations of the determination section 3 and the classification section 4. For example, consider a case in which defect type A can be further divided into either of defect type A1 and defect type A2. That is, consider a case in which the defect type can be divided into any of defect type A1, defect type A2 and defect type B. In this case, first in the determination section 3, a discriminant function, which indicates a decision boundary for classifying to which of defect type A and defect type B the defect type of a defect to be classified belongs, is determined by the above described procedure. The classification section 4 classifies to which of defect type A and defect type B the defect type of a defect to be classified belongs by using the discriminant function determined by the determination section 3. Next, in the determination section 3, a discriminant function, which indicates a decision boundary for classifying to which of defect type A1 and defect type A2 the defect type of the defect to be classified which has been classified to be defect type A belongs, is determined by the same procedure as described above. The classification section 4 classifies to which of defect type A1 and defect type A2 the defect type of the defect to be classified, which has been classified to be defect type A belongs by using the discriminant function determined in the determination section 3. As a result, the defect to be classified is classified into any of three defect types A1, A2 or B. By repeating a procedure similar to the above described procedure, it is possible to classify to which of four or more defect types the defect type of a defect to be classified belongs.

Figure 4:
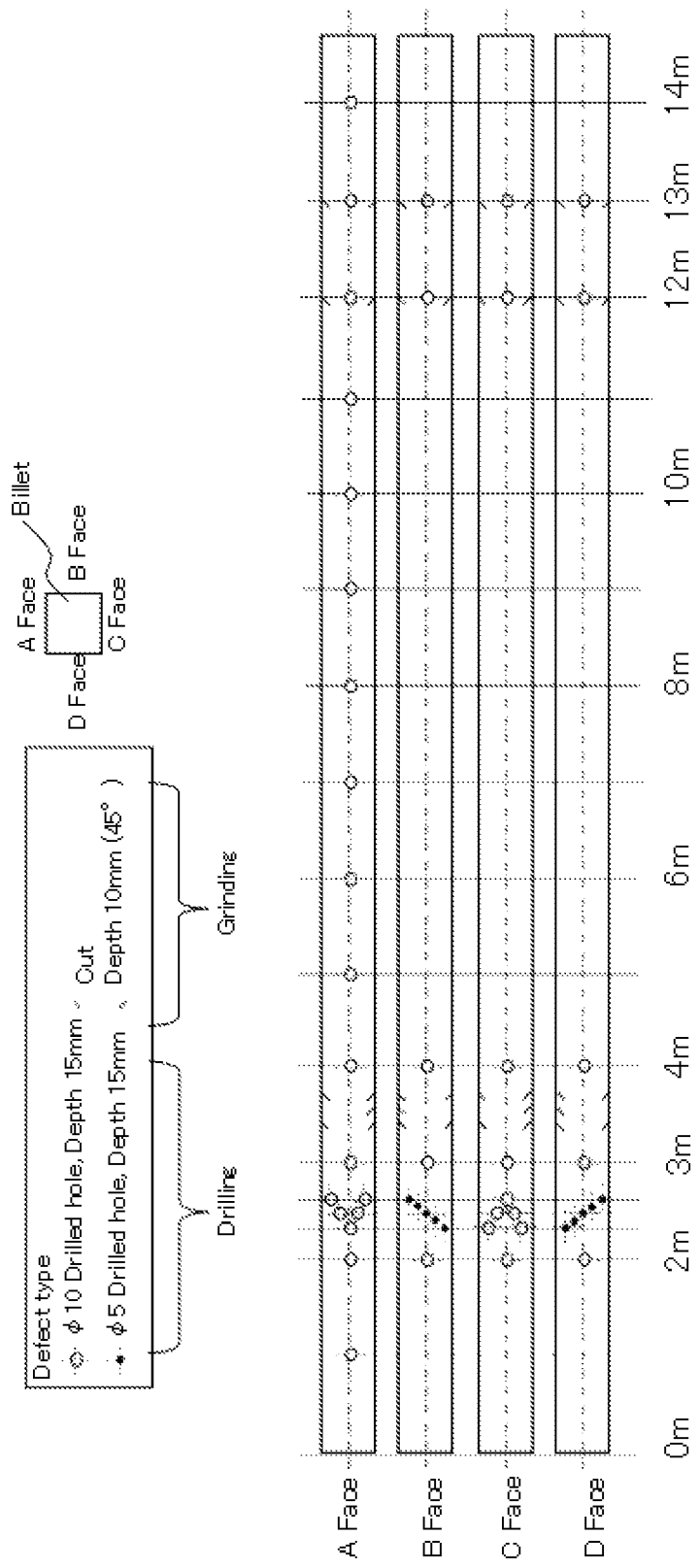
FIG. 4 is a diagram showing a billet used for a classification test of defect types.

As shown in FIG. 1B, a defect classification apparatus 1 of the present embodiment was placed on the downstream side of the finish rolling mill 5 of a hot rolling line and a classification test of defect type was conducted. To be specific, as shown in FIG. 4, two billets (each of which weighs 2 ton) which had artificial cracks formed by a drill and a grinder in priori were rolled into two wire rods each having a wire diameter of 20 mm and 13 mm, and an online test was conducted to classify whether a defect which occurred in the foregoing procedure was classified into defect type A or defect type B. Moreover, as shown in FIG. 1B, a through-type differential eddy-current testing apparatus 6 as well was placed on the downstream side of the finish rolling mill of the hot rolling line and on the upstream side of the defect classification apparatus 1 of the present embodiment. Note that the surface temperature of a rolling product of which image sequence was grabbed by a camera 2 was around 1000° C.

Defect type A was rubbing mark on the surface of the wire rod, and defect type B was a crack which occurred on the surface of the wire rod. The defect classification apparatus 1 of the present embodiment classified that 45 defects categorized to defect type B, that is, a crack, among the defects that occurred in the wire rod having a wire diameter of 20 mm, and 23 defects categorized to defect type B, that is, a crack, among the defects that occurred in the wire rod having a wire diameter of 13 mm. On the other hand, the through-type differential eddy-current testing apparatus 6 was only able to detect 31 cracks in the wire rod having a wire diameter of 20 mm, and 15 cracks in the wire rod having a wire diameter of 13 mm.

The two wire rod coils having wire diameters of 20 mm and 13 mm respectively, which were wound up after rolling, were each cut into lengths of 50 mm and were subjected to an offline magnetic powder testing to verify cracks. As a result of that, there were 44 cracks in the wire rod having a wire diameter of 20 mm, and 22 cracks in the wire rod having a wire diameter of 13 mm.

In the defect classification apparatus 1 of the present embodiment, although one incidence of over-detection occurred both in the two wire rods having wire diameters 20 mm and 13 mm respectively, it was possible to judge that all the cracks including those that were not detected by the through-type differential eddy-current testing apparatus 6 categorized to defect type B in an online inspection.

From what has been described above, it is made clear that the defect classification apparatus 1 of the present embodiment can accurately classify the defect type of a defect.

Figure 5:
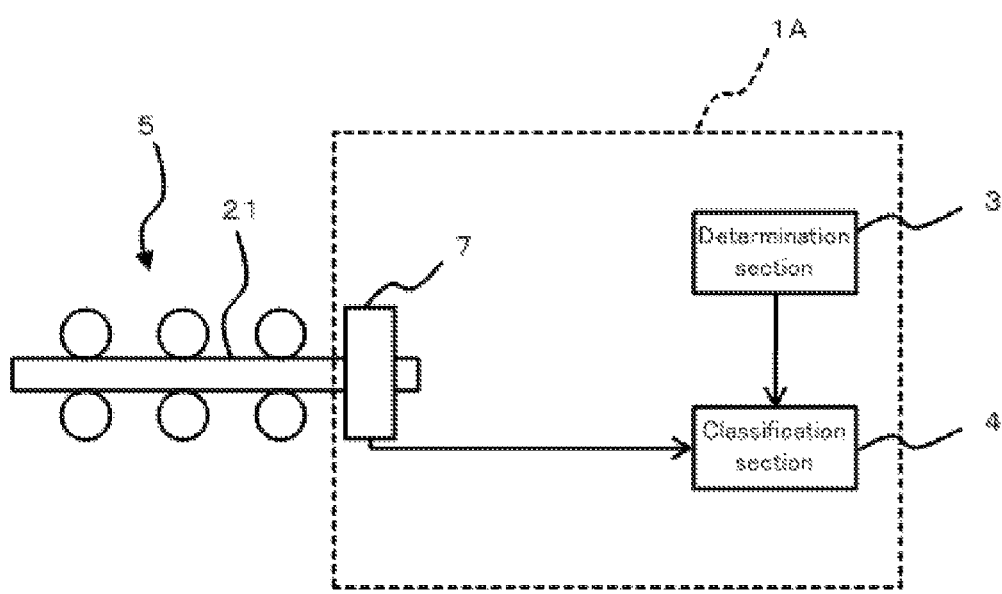
FIG. 5 is a schematic configuration drawing of a defect classification apparatus relating to another embodiment of the present invention.

Note that in the present embodiment, although description has been made by way of an example where an image capture device (a camera 2 and a light source) is provided as the extraction section for extracting features, and the defect type is classified by using the features extracted by performing image processing on a grabbed image sequence of a rolling product, the defect classification apparatus relating to the present invention will not be limited to such an embodiment, and may be configured as shown in FIG. 5.

FIG. 5 is a schematic configuration drawing showing a defect classification apparatus 1A relating to another embodiment of the present invention. As shown in FIG. 5, the defect classification apparatus 1A relating to the present embodiment includes an extraction section 7, a determination section 3, and a classification section 4. The extraction section 7 comprises at least one of an image capture device for a rolling product, an eddy-current testing apparatus for performing eddy current testing on a rolling product, and an ultrasonic testing apparatus for performing ultrasonic testing on a rolling product. The classification section 4 is configured to classify the defect type of a defect to be classified which occurs in a rolling product by using at least one kind of features among the features extracted by performing image processing on a grabbed image sequence of the rolling product grabbed by the image capture device, the features extracted by performing eddy-current testing on the rolling product with the eddy-current testing apparatus, and the features extracted by performing ultrasonic testing on the rolling product with the ultrasonic testing apparatus.

REFERENCE SIGNS LIST

1 Defect classification apparatus
2 Camera
3 Determination section
4 Classification section
7 Extraction section

The invention claimed is:

1. A defect classification apparatus in which a data point indicating feature information whose components include a plurality of features indicating attributes of a defect to be classified having an unknown defect type is mapped to a point in a mapping space which has a dimensional number higher than the number of the features constituting the feature information, and determination is made as to which of two regions of defect type, which are formed by separating the mapping space, contains the mapped point to classify the defect type of the defect to be classified to be the defect type corresponding to the region where the mapped point is located, the defect classification apparatus comprising:

an extraction section for extracting the features; a determination section for determining a discriminant function indicating a decision boundary which separates the mapping space; and a classification section for classifying the defect type of the defect to be classified based on an output value of the discriminant function when the feature information of the defect to be classified is inputted into the discriminant function determined by the determination section; wherein each of the two defect types is a predetermined and mutually different defect type, the determination section determines the discriminant function by using the feature information of a training defect dataset which is known to have either of the two defect types, the discriminant function is a function that consists of a kernel function (x, x') which outputs a mapped point of a training defect dataset whose feature information is inputted when feature information of the training defect dataset of either one or the other defect type of the two defect types is inputted, and the weight of each feature constituting the feature information, which is attached to the kernel function k(x, x'), and the kernel function (x, x') is a kernel function in which a matrix K whose elements are given as k(x, x') is positive semi-definite, x is feature information of the training defect dataset of the one defect type, and x' is feature information of the training defect dataset of the other defect type, wherein the determination section:

determines the weight of each feature constituting the feature information for a predetermined regularization parameter so as to minimize the value of an error function, which consists of a sum of: classification error which is defined by the difference between the output value of the discriminant function when the feature information of a training defect dataset of the one defect type is inputted into the kernel function k(x, x') and the value corresponding to the one defect type, and the difference between the output value of the discriminant function when the feature information of a training defect dataset of the other defect type is inputted into the kernel function k(x, x') and the value corresponding to the other defect type, decreases as the absolute value of either of the two differences decreases, and increases as the absolute value increases; and a regularization term multiplied by the regularization parameter, the regularization term has a positive correlation with the dimensional number of the discriminant function, and varies according to the weight of each feature constituting the feature information, and when the weight of each feature constituting the feature information which has been determined to minimize the value of the error function is temporarily adopted as the weight of each feature constituting the discriminant function, if the number of misclassification, which is the sum of the number of training defect dataset of the one defect type, for which the absolute value of the difference between the output value of the discriminant function when the feature information of a training defect dataset of the one defect type is inputted into the kernel function k(x, x') and the value corresponding to the other defect type is smaller than the absolute value of the difference between the output value of the discriminant function when the feature information of a training defect dataset of the one defect type is inputted into the kernel function k(x, x') and the value corresponding to the one defect type, and the number of training defect dataset of the other defect type for which the absolute value of the difference between the output value of the discriminant function when the feature information of a training defect dataset of the other defect type is inputted into the kernel function k(x, x') and the value corresponding to the one defect type is smaller than the absolute value of the difference between the output value of the discriminant function when the feature information of a training defect dataset of the other defect type is inputted into the kernel function k(x, x') and the value corresponding to the other defect type, is not less than a predetermined value; adjusts the regularization term parameter to determine the weight of each feature constituting the feature information again so as to minimize the value of the error function, and if the number of misclassification is less than the predetermined value; ascertains that the weight of each feature constituting the feature information which has been determined so as to minimize the value of the error function is adopted as the weight of each feature constituting the discriminant function to determine the discriminant function.

2. The defect classification apparatus according to claim 1, wherein
at least the extraction section is placed in a rolling line of a rolling product, and a defect type of a defect to be classified which occurs in the rolling product is classified.

3. The defect classification apparatus according to claim 2, wherein
at least an image capture device for a rolling product as the extraction section is placed in the rolling line along with an eddy-current testing apparatus, and
a defect type of a defect to be classified, which occurs in the rolling product is classified by using a feature extracted by performing image processing on a grabbed image sequence of the rolling product grabbed by the image capture device.

4. The defect classification apparatus according to claim 2, wherein
the extraction section comprises at least one of an image capture device for the rolling product, an eddy-current testing apparatus for performing eddy-current testing on the rolling product, and an ultrasonic testing apparatus for performing ultrasonic testing on the rolling product, and
a defect type of a defect to be classified which occurs in the rolling product is classified by using at least one kind of features among the features extracted by performing image processing on a grabbed image sequence of the rolling product grabbed by the image capture device, the features extracted by performing eddy-current testing on the rolling product with the eddy-current testing apparatus, and the features extracted by performing ultrasonic testing on the rolling product with the ultrasonic testing apparatus.

* * * * *